(12) United States Patent
Lim et al.

(10) Patent No.: US 7,070,598 B2
(45) Date of Patent: Jul. 4, 2006

(54) MINIMALLY INVASIVE EXPANDING SPACER AND METHOD

(75) Inventors: Roy Lim, Memphis, TN (US); Kevin T. Foley, Germantown, TN (US); Michael C. Sherman, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 95 days.

(21) Appl. No.: 10/817,024

(22) Filed: Apr. 2, 2004

(65) Prior Publication Data

US 2004/0193158 A1    Sep. 30, 2004

Related U.S. Application Data

(63) Continuation-in-part of application No. 10/178,960, filed on Jun. 25, 2002.

(51) Int. Cl.
*A61B 17/80* (2006.01)
(52) U.S. Cl. ...................... 606/61; 623/17.16
(58) Field of Classification Search ............... 606/61, 606/69, 70, 71, 90, 105, 198, 208; 623/17.16; 433/7; 600/222
See application file for complete search history.

(56) References Cited

U.S. PATENT DOCUMENTS

| | | |
|---|---|---|
| 5,171,278 A | 12/1992 | Pisharodi |
| 5,235,966 A | 8/1993 | Jamner |
| 5,390,683 A | 2/1995 | Pisharodi |
| 5,522,899 A | 6/1996 | Michelson |
| 5,599,279 A | 2/1997 | Slotman et al. |
| 5,620,458 A | 4/1997 | Green et al. |
| 5,658,335 A | 8/1997 | Allen |
| 5,665,122 A | 9/1997 | Kambin |
| 5,697,889 A | 12/1997 | Slotman et al. |
| 5,782,832 A | 7/1998 | Larsen et al. |
| 5,865,848 A | 2/1999 | Baker |
| 5,888,224 A | 3/1999 | Beckers et al. |
| 6,039,761 A | 3/2000 | Li et al. |
| 6,045,579 A | 4/2000 | Hochshuler et al. |
| 6,080,193 A | 6/2000 | Hochshuler et al. |
| 6,102,950 A | 8/2000 | Vaccaro |
| 6,126,689 A | 10/2000 | Brett |
| 6,127,597 A | 10/2000 | Beyar et al. |
| 6,174,334 B1 | 1/2001 | Suddaby |
| 6,176,882 B1 | 1/2001 | Biedermann et al. |
| 6,179,873 B1 | 1/2001 | Zientek |

(Continued)

FOREIGN PATENT DOCUMENTS

DE    200 04 812 U1    11/2000

(Continued)

*Primary Examiner*—David O. Reip
(74) *Attorney, Agent, or Firm*—Coats & Bennett, P.L.L.C.

(57) ABSTRACT

A minimaly invasive spacer for positioning between vertebral members. The spacer is adjustable between a first orientation having a reduced size to facilitate insertion between the vertebral members. A second orientation has an enlarged size for contacting the vertebral members. The spacer includes linkages that are attached to a pair of plates. A pull arm is operatively connected to the linkages for adjusting the spacer from the first orientation to the second orientation. A delivery device is attached to the spacer for insertion between the vertebral members. In one embodiment, the delivery device is detachable to be removed from the spacer once positioned between the vertebral members. Methods of using the spacer include positioning the spacer between the vertebral members while in the first orientation. The spacer is then enlarged to the second orientation, and the delivery device is removed with only the spacer remaining within the patient.

19 Claims, 8 Drawing Sheets

U.S. PATENT DOCUMENTS

| | | |
|---|---|---|
| 6,183,517 B1 | 2/2001 | Suddaby |
| 6,190,414 B1 | 2/2001 | Young et al. |
| 6,193,757 B1 | 2/2001 | Foley et al. |
| 6,217,579 B1 | 4/2001 | Koros |
| 6,332,895 B1 | 12/2001 | Suddaby |
| 6,582,451 B1 | 6/2003 | Marucci et al. |
| 2003/0220650 A1 | 11/2003 | Major et al. |

FOREIGN PATENT DOCUMENTS

| | | |
|---|---|---|
| EP | 0 676 176 A1 | 10/1995 |
| WO | WO 95/25485 | 9/1995 |
| WO | WO 97/00054 | 1/1997 |
| WO | WO 01/41652 | 6/2001 |

MINIMALLY INVASIVE EXPANDING SPACER AND METHOD

This application is a continuation-in-part of previously filed U.S. patent application Ser. No. 10/178,960 filed on Jun. 25, 2002.

BACKGROUND

Various devices are used for controlling the spacing between vertebral members. These devices may be used on a temporary basis, such as during surgery when it is necessary to access the specific surfaces of the vertebral member. One example includes preparing the endplates of a vertebral member. The devices may also remain permanently within the patient to space the vertebral members.

It is often difficult to position the device between the vertebral members in a minimally invasive manner. A device that is small may be inserted into the patient and between the vertebral members in a minimally invasive manner. However, the small size may not be adequate to effectively space the vertebral members. A larger device may be effective to space the vertebral members, but cannot be inserted into the patient and between the vertebral members in a minimally invasive manner.

SUMMARY

The present invention is directed to a minimally invasive spacer for spacing vertebral members. The spacer is positionable between a closed orientation to fit between the vertebral members. The spacer may be expanded to a variety of sizes larger than the closed orientation to space the vertebral members as desired. In one embodiment, the spacer may be locked in the open configuration.

The spacer is a mechanical device having a pair of plates that contact the vertebral members. In one embodiment, both plates move outward from a centerline of the device. In another embodiment, only one of the plates moves outward from the centerline.

Linkages are positioned between and pivotally attached to the plates. A link angle is formed by the linkages and the centerline of the device. The linkages move from a closed orientation having a first link angle to a variety of open orientations each having a link angle greater than the first link angle.

In one embodiment, linkages are paired together between the plates. A first end of the linkages is attached to the first plate, and a second end is attached to the second end. The linkages are attached together about the centerline of the device. In one embodiment, a complimentary pair of linkages are adjacently positioned to the first link pair. The complimentary linkage pairs may each include toothed-ends that mate together when the spacer moves from the closed orientation to the open orientation.

A pull arm is positioned within the spacer to apply an axial force to the linkages. The pull arm is pivotally connected to the linkages. As the pull arm moves, linkages that are pivotally connected move outward thus increasing the height of the spacer. A variety of different devices may be used for applying an axial force to the pull arm.

A delivery device may be used for positioning the spacer between the vertebral members. The delivery device may be permanently attached to the spacer such that both the spacer and delivery device are removed after completion of the procedure. In another embodiment, the delivery device is removably connected to the spacer and can be removed from the patient leaving the spacer between the vertebral members. In one embodiment, the delivery device may be reattached to the spacer. Once delivered between the vertebral members and the spacer is deployed, the delivery device may be disconnected and removed to give the surgeon more space. Once completed with the procedure, the delivery device may be reattached to remove the spacer. Prior to removal, the spacer may be returned towards the closed orientation.

DETAILED DESCRIPTION

Figure 1:
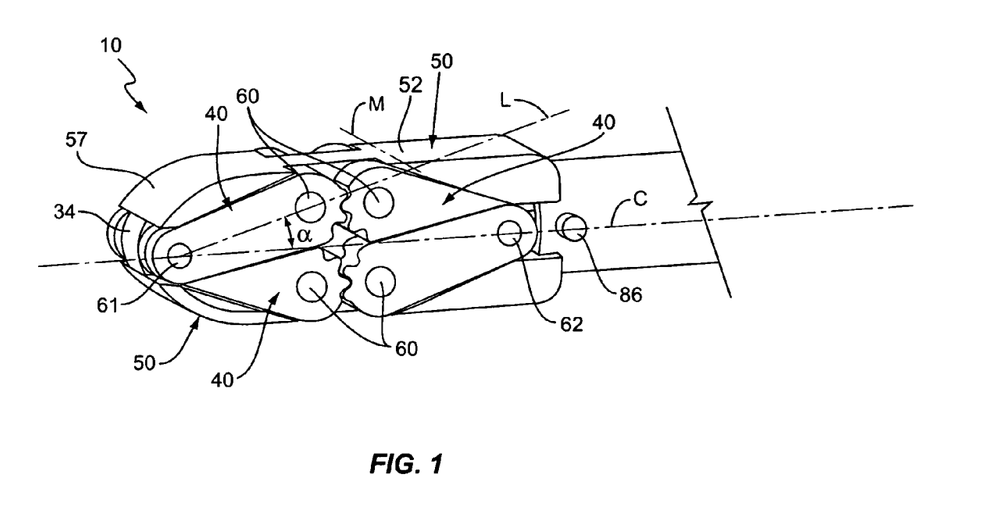
FIG. 1 is a perspective view of a spacer in a closed orientation according to one embodiment of the present invention.
Figure 2:
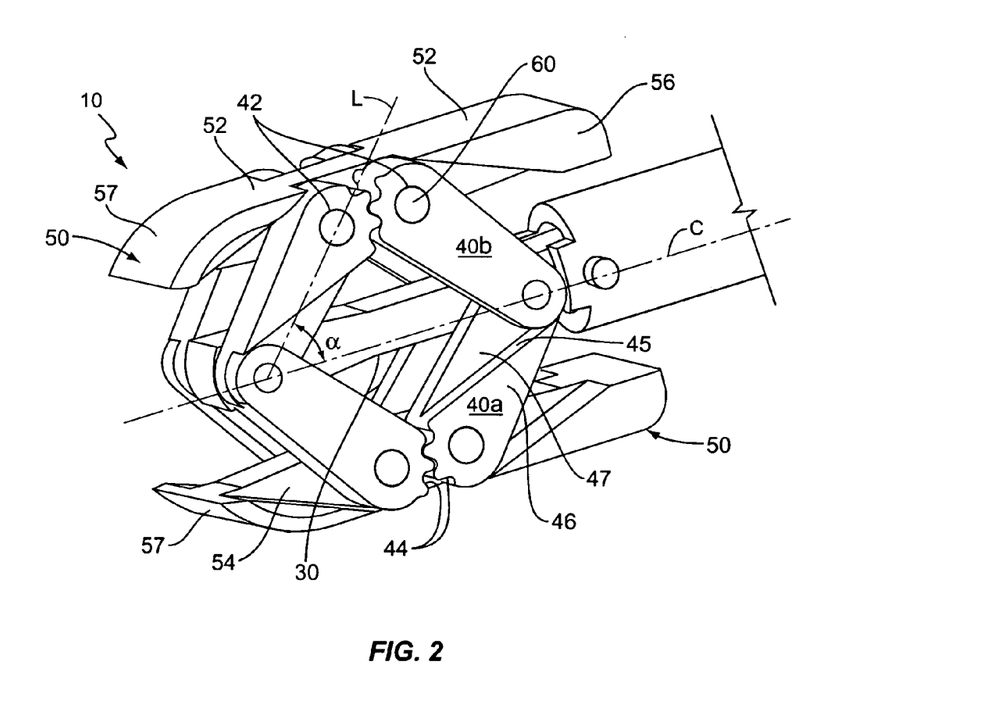
FIG. 2 is a perspective view of a spacer in an opened orientation according to one embodiment of the present invention.

The present invention is directed to a minimally invasive spacer, generally illustrated as 10, for positioning between vertebral members. The spacer 10 is adjustable between a variety of sizes between a first orientation and a second orientation. The first orientation is illustrated in FIG. 1 and has a reduced size to facilitate insertion into the patient and between the vertebral members. A second orientation, as illustrated in FIG. 2, has an enlarged size for contacting and spreading the vertebral members. The spacer 10 includes linkages 40 attached to a pair of plates 50. A pull arm 30 operatively connects to the linkages 40 to adjust the spacer 10 at positions between the first orientation and the second orientation. A delivery device 80 is attached to the spacer 10 to deliver the spacer 10 between the vertebral members. The delivery device 80 may be detachable to be removed from the spacer 10 once positioned between the vertebral members.

Spacer 10 may include a number of linkages 40 positioned between the plates 50 depending upon the application. Each individual linkage 40 mates with a complimentary linkage 40 to provide movement to the spacer 10. In embodiments illustrated in FIGS. 1 and 2, spacer 10 includes two pairs of linkages 40 on a first side of the pull arm 30, and another two pairs of linkages 40 on a second side of the pull arm 30 for a total of four pairs of linkages, or eight total linkages. In another embodiment (not illustrated), spacer 10 includes only two pairs of linkages 40, or four total linkages. Various numbers of linkages 40 may be included within the present invention depending upon the specific requirements of the spacer and necessary amount of disc space load. In one embodiment, linkages 40 are independent and individually spaced apart. In another embodiment, linkages 40 are paired together, but adjacent linkage pairs do not contact.

Figure 6:
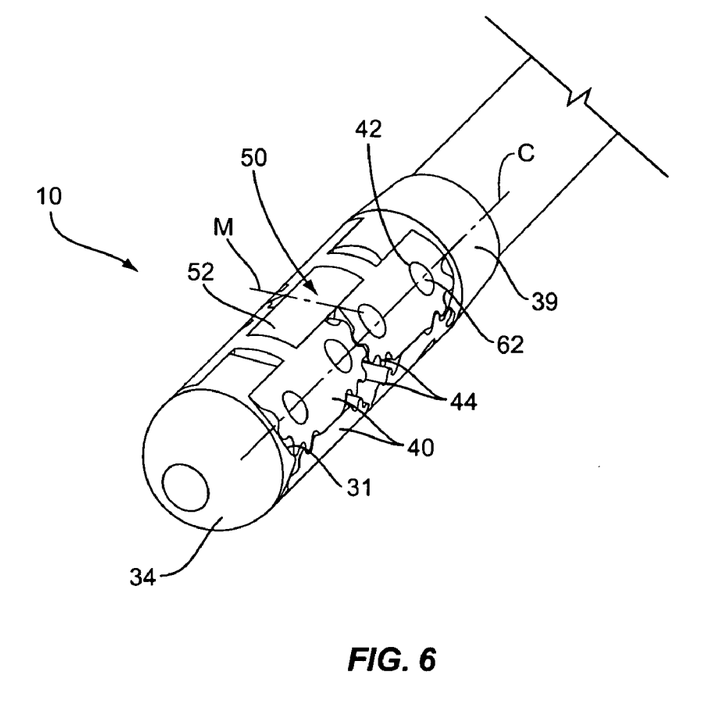
FIG. 6 is a perspective view of another embodiment of the spacer in a closed orientation.
Figure 7:
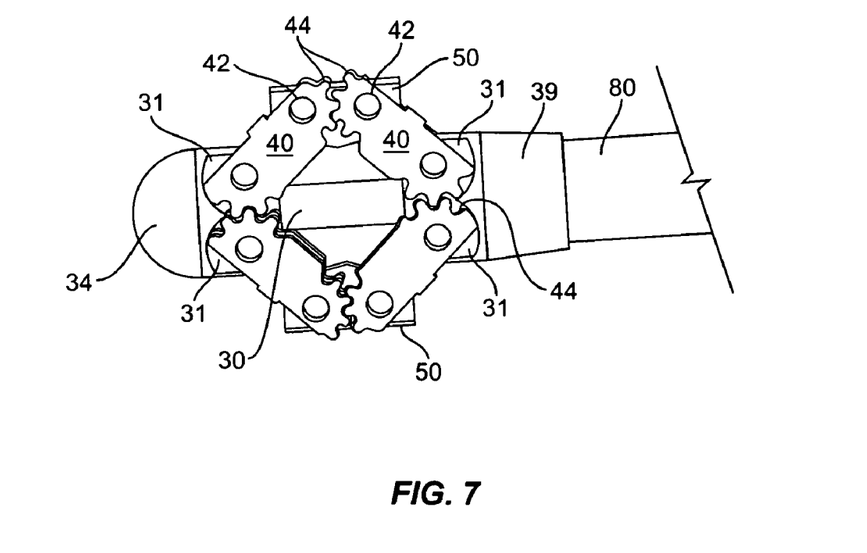
FIG. 7 is a perspective view of another embodiment of the spacer in an open orientation.

Each linkage 40 has an elongated shape with an aperture 42 adjacent to each end to receive pins. The ends of each linkage 40 may have a variety of shapes and configurations. In embodiments illustrated in FIGS. 1 and 2, each end is substantially rounded. In the embodiments illustrated in FIGS. 6 and 7, each end has a partially rounded section with a linear edge extending along one side of the linkage 40. In one embodiment, teeth 44 are positioned about at least one end of each linkage 40. Teeth 44 are sized to mate with complimentary teeth 44 on adjacent linkages 40. Teeth 44 may be positioned along the ends of the linkages 40, or may also extend along the elongated length. In the embodiments illustrated in FIGS. 1 and 2, teeth 44 are positioned along one side of the rounded edge. In the embodiments of FIGS. 6 and 7, teeth 44 extend along only a section of each end and further down along the length.

In one embodiment, linkages 40 are shaped to compliment adjacent linkages. In one embodiment illustrated in FIG. 2, a linkage first side 40a includes a recessed section 47 and an extended section 46. An edge 45 extends across the length of the linkage 40 defining the recessed section 47 and extended section 46. A linkage second side 40b may have a variety of configurations, such as substantially flat. The linkages 40 overlap with the first sides 40a mating together in the closed orientation. The complimentary shapes give the linkages 40 a smaller profile thus reducing the dimensions of the spacer 10 as illustrated in FIG. 1.

Plates 50 are positioned on a first and second side of the spacer 10 to contact the vertebral members. Plates 50 include a contact surface 52 having a surface area to distribute the disc space load created by the spacer 10 across a large region of the vertebral members. In one embodiment, the contact surface 52 is about 16 mm in length by about 8 mm in width. The dimensions of the contact surface 52 may vary depending upon the construction of the spacer 10. By way of example, embodiments illustrated in FIGS. 1 and 2 have a contact surface 52 with a substantially hourglass shape. In embodiments illustrated in FIGS. 6 and 7, contact surface 52 has a substantially rectangular shape. In embodiments illustrated in FIGS. 1 and 2, the contact surface 52 is substantially flat. In another embodiment, the contact surface 52 may be rounded. In one embodiment, plate 50 has a width equal to the overall width of the spacer 10. In another embodiment, plate 50 has a width less than the overall width of the spacer 10.

Linkages 40 may connect to the plates 50 in a number of different positions. In one embodiment, an edge 56 of contact surface 52 has a width for receiving an aperture for receiving a pin. In embodiments illustrated in FIGS. 1 and 2, plates 50 include an outwardly extending rib 54. Rib 54 is sized with an aperture therein to receive the pin.

In one embodiment, plate 50 includes a front 57 which is angled or rounded inward relative to the contact surface 52. In one embodiment, front 57 has a length such that distal ends of the first and second plates 50 contact each other in the closed orientation. In another embodiment, front 57 extends a lesser distance to cover only a portion of the linkages 40 and pull arm 30 when in the closed orientation.

Figure 3:
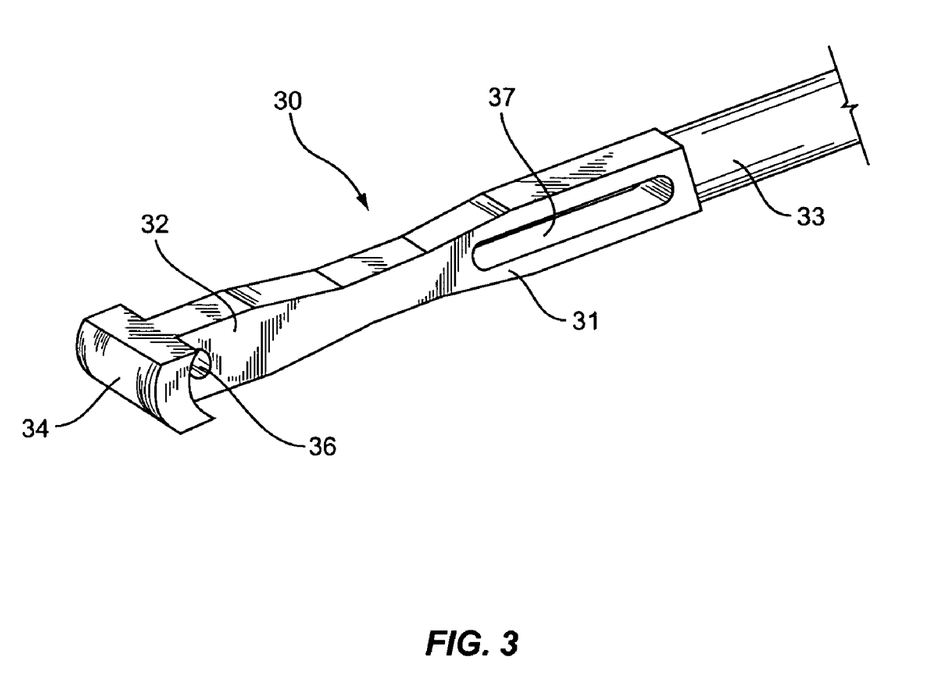
FIG. 3 is a perspective view of a pull arm according to one embodiment of the present invention.

Pull arm 30 moves the linkages 40 from the closed orientations through the open orientations. One embodiment of the pull arm 30 is illustrated in FIG. 3 and includes an elongated body having an aperture 36 and a slot 37 for receiving pins. A nose 34 on the distal end may have a rounded or angled shape. As illustrated in FIG. 1, the rounded or angled shape facilitates insertion of the spacer 10 between the vertebral members. In one embodiment as illustrated in FIG. 3, pull arm 30 includes a distal section 31 and a proximal section 33 that are detachable. When the device 80 is detached from the spacer 10, proximal section 33 detaches from the distal section 31. The spacer 10, including the pull arm distal section 31, remains as the delivery device 80 and proximal pull arm 33 are removed. The pull arm 30 may extend through only a portion of the delivery device 80, or may extend through the entire length.

Figure 14:
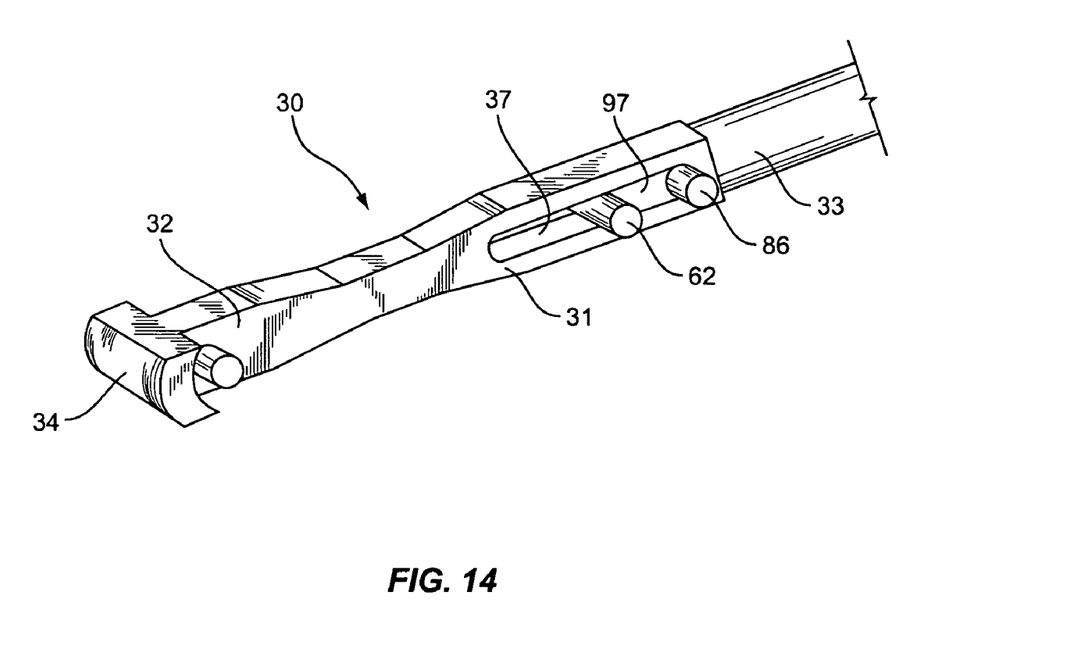
FIG. 14 is a perspective view of an alternative embodiment with a push link within the slot of the pull arm.

Pins are positioned within the spacer 10 to connect together the linkages 40, pull arm 30, and plates 50. As illustrated in FIG. 1, pins 60 extend through the linkages 40 and plate 50. Pin 61 extends through the linkages 40 and aperture 36 in the pull arm 30 at the distal end of the spacer. Pin 62 extends through the linkages 40 and slot 37 in the pull arm 30. Pins 60, 61, and 62 may have a variety of diameters and sizes depending upon the specific application of the spacer 10. In one embodiment, pin 62 and pin 86 are constructed from a single push link 97 as illustrated in FIG. 14. In one embodiment, each pin has a diameter of about 1.33 mm. The term "pin" used herein is broadly used as a means for pivotally attached two or more members. One skilled in the art will understand that various other similar devices may serve this same function and are considered within the scope of the present invention.

As illustrated in FIG. 1, in the closed orientation the spacer 10 has a bullet-like configuration. The plates 50, linkages 40, and pull arm 30 combine together to form a rounded or angled front which eases the insertion of the spacer 10 in the patient. In one embodiment, the contact surfaces 52 are symmetric about a centerline C, i.e., have the same orientation relative to the centerline. In one embodiment, the contact surfaces 52 of the plates 50 are parallel with the centerline C when the spacer 10 is in the closed orientation. In one embodiment, the spacer 10 in the closed orientation has a length of between about 22–24 mm, width of about 8 mm, and a height of about 7 mm.

As illustrated in FIG. 2, the spacer 10 in the open configuration has a larger height. The height may be adjusted depending upon the angle of the linkages 40 relative to the centerline C. The spacer 10 may be expanded to a variety of different sizes and heights and the term "open configuration" is used to indicate any of these orientations. In one embodiment, when the spacer 10 is expanding from the closed orientation, the contact surfaces 52 remain symmetrical about the centerline C. In one embodiment, both plates 50 move equal amounts such that the distance between the centerline C and the contact surface is the same for each plate 50. In another embodiment, one plate 50 moves a greater amount than the corresponding plate 50. In another embodiment, one plate 50 is fixed and the corresponding plate 50 move outward to increase the height of spacer 10.

Figure 4:
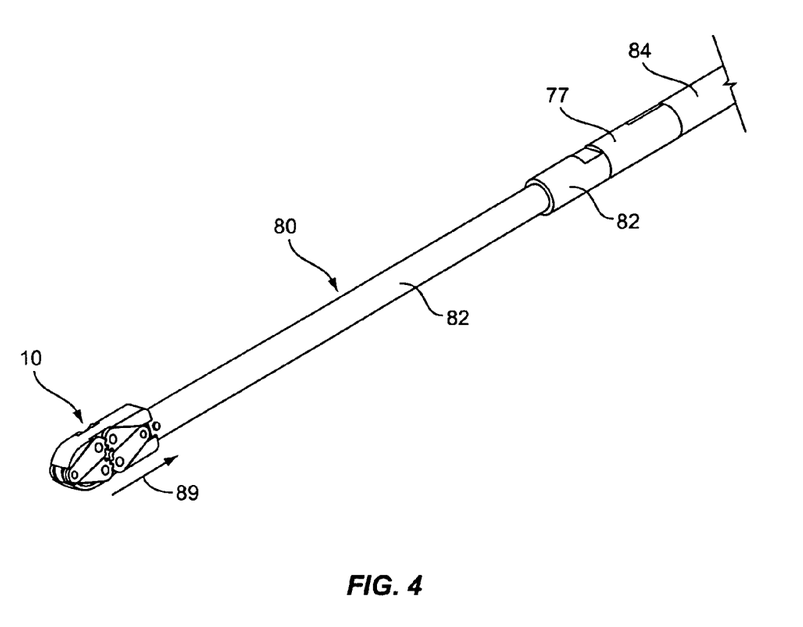
FIG. 4 is a is a perspective view of one embodiment of the spacer and attached delivery device constructed according to one embodiment of the present invention.

A variety of different delivery devices 80 may be used for positioning the spacer 10 between the vertebral members. One embodiment is illustrated in FIG. 4 and includes an elongated rod attached to the proximal end of the spacer 10. In one embodiment, the delivery device is hollow and surrounds at least a portion of the pull arm 30. Delivery device 80 may have a variety of cross-sectional shapes and sizes depending upon the application. Delivery device 80 may be constructed of a single elongated member, or may be constructed of different sections such as first section 82 and second section 84.

Delivery device 80 may be attached to the spacer 10 in a number of different manners. In one embodiment as illustrated in FIG. 1, pin 86 extends through the device 80 and the slot 37 within the pull arm 30 to connect the spacer 10 to the device 80. In one embodiment, a push link 97 has a first pin 62 that connects to the proximal linkages 40a, 40b, and a second pin 86 that connects to the delivery device 80. In another embodiment, the delivery device 80 is permanently attached to the spacer 10. In another embodiment, the pull arm 30 is also the delivery device 80.

In one embodiment, the spacer 10 is inserted via the delivery device 80 between the vertebral members and removed upon completion of the procedure. In one embodiment, the spacer 10 is removed from the delivery device 80 and remains within the patient. The spacer 10 may remain permanently within the patient, or in one embodiment, after the spacer is detached and the surgeon completes the procedure, the delivery device 80 is reattached to remove the spacer 10. In one embodiment, pin 86 is broken to remove the device 80 from the spacer 10. In one embodiment as illustrated in FIG. 3, pull arm 30 includes a distal section 31 and a proximal section 33 that are detachable. When the device 80 is detached from the spacer 10, proximal section 33 detaches from the distal section 31. The spacer 10, including the pull arm distal section 31, remains as the device 80 and proximal pull arm 33 are removed.

In one manner of use, spacer 10 is connected to the distal end of the delivery device 80. While in the closed orientation, the spacer 10 is positioned within the patient between adjacent vertebral members. In one embodiment, the spacer 10 is positioned within the disc space between the adjacent vertebral members and contacts the end plates of the vertebral members upon expansion. Once positioned, an axial load or deployment force is applied to the pull arm 30 to force the pull arm 30 inward in the direction of arrow 89 in FIG. 4. Axial movement results in the linkages 40 pivoting outward from the closed position in the embodiment of FIG. 1 towards the open orientation in the embodiment of FIG. 2. The teeth 44 of opposing linkages 40 mate together during the movement with the plates 50 moving outward from the centerline C. In one embodiment, each of the two plates 50 move equal amounts and are symmetric about the centerline C.

As the linkages 40 expand outward and the pull arm 30 moves inward, pin 62 slides along the distal arm slot 37 as the spacer 10 moves from the closed to open orientations. Pin 61 is mounted within linkages 40 and the pull arm aperture 36 and does not move relative to the pull arm 30. In the closed orientation illustrated in FIG. 1, pin 61 is spaced apart from pin 62 a distance greater than in the open orientation as illustrated in FIG. 2. The amount of axial movement of the pull arm 30 results in the amount of deployment of the spacer 10. The spacer 10 may be opened to any distance between the closed and open orientations depending upon the specific application.

An axial force is applied to the pull arm 33 to deploy the spacer 10 to the open position. The power mechanism to apply the force may be within the spacer 10, or delivery device 80. In one embodiment, the axial force is applied by linearly moving the pull arm 30. In one embodiment, section 84 is attached to the proximal pull arm 33. The section 84 can be locked in the extended position away from the first section 82 to lock the spacer 10 in the open orientation. In one embodiment, a scroll 77 is threaded onto the distal end of the second section 84 adjacent to the first section 82 as illustrated in FIG. 4. Section 84 and scroll 77 are distanced from section 82 thereby applying force to the pull arm 30 and expanding the distractor 10. Scroll 77 can be threaded distally along the second section 84 to contact the first section 82 and lock the distractor 10 in an opened position. To close the distractor 10, scroll 77 is threaded proximally along the second section 84. In one embodiment, scroll 77 is knurled to allow rotation of the scroll 77 by hand.

Figure 5:
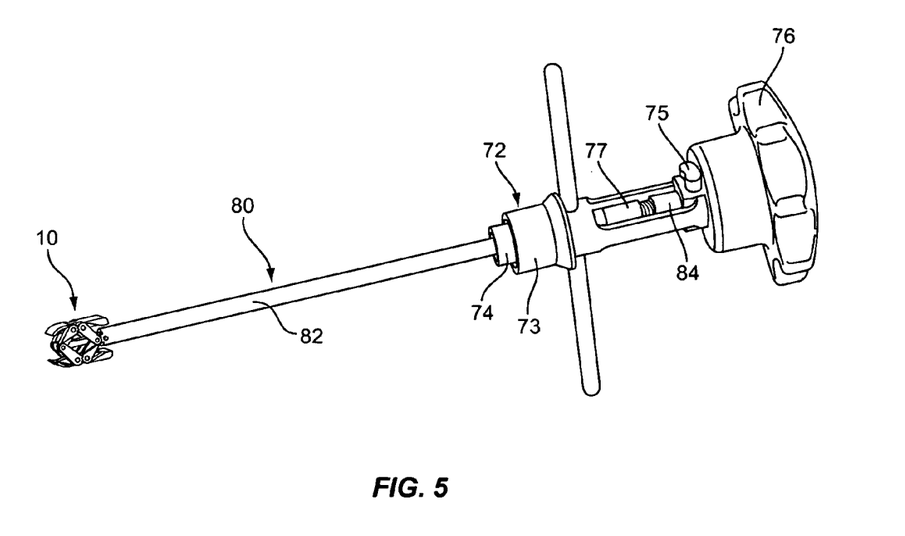
FIG. 5 is a perspective view of one embodiment of the spacer, delivery device, and force mechanism constructed according to one embodiment of the present invention.

A mechanism for applying an axial force to the pull arm 30 may have a variety of configurations. The mechanism may be positioned adjacent to the spacer 10, or positioned distant from the spacer 10 to be outside the patient. In one embodiment illustrated in FIG. 5, a power mechanism is attached to the delivery device 80 to apply an axial force. Power mechanism includes a quick release mechanism 72 at the distal end of power mechanism to attach to the delivery device first section 82. In one embodiment, quick release mechanism 82 includes a spring-biased collar 73 positioned around a receptacle 74. Collar 73 may be pulled back to load the first section 82 within the receptacle 74. Releasing the collar 73 causes the receptacle 74 to contract and lock the first section 82. In one embodiment, quick release mechanism 72 includes one or more balls that engage in grooves in the first section 82. In one embodiment, a slide lock 75 attaches to the second section 84. Torque is applied to a handle 76 causing the scroll 77 and second section 84 to separate from the first section 82 thus applying an axial force to the pull arm 30 and opening the distractor 10. At the desired orientation, scroll 77 is threaded distally to contact the first section 82 and lock the distractor 10. Once locked, the power mechanism 70 can be removed from the delivery device 80 for more working space for the surgeon.

A linkage axis L is formed by the line extending through the linkage 40. In embodiments illustrated in FIGS. 1 and 2, linkage axis L extends through the points of intersection with the plate 50 and pull arm 30. A link angle α is formed by the linkage axis L and the centerline C. In the embodiment illustrated in FIG. 1, the link angle α is greater than zero when the spacer 10 is in the closed orientation. In one embodiment, a link angle α greater than 0° in the closed orientation has been determined to facilitate opening the spacer 10.

The axial force, or required deployment force, necessary to open the spacer 10 changes during the expansion process. Additionally, the force applied by the spacer 10 on the vertebral members during the expansion process, or allowable disc space load, changes during the expansion process. Stated in another manner using a 3-coordinate geometry having coordinates x, y, and z, the axial force is the force in the x direction and the vertebral member load is the force in the y direction.

In one embodiment, the spacer 10 is positionable between a closed orientation having a height of about 7 mm and a link angle a of about 16°, and an open configuration having a height of about 14 mm and a link angle a of about 49°. The following chart illustrates the parameters of the spacer 10 at the various stages of deployment:

| Height h (mm) | Link Angle θ (rads) | Link Angle θ (degrees) | Required Deployment Force (lbf) | Allowable Disc Space Load (lbf) |
|---|---|---|---|---|
| 7 | 0.29 | 16.61 | 541.15 | 322.79 |
| 7.5 | 0.33 | 18.63 | 535.12 | 360.76 |
| 8 | 0.36 | 20.67 | 528.34 | 398.74 |
| 8.5 | 0.40 | 22.75 | 520.77 | 436.71 |
| 9 | 0.43 | 24.85 | 512.40 | 474.69 |
| 9.5 | 0.47 | 27.00 | 503.17 | 512.66 |
| 10 | 0.51 | 29.18 | 493.04 | 550.64 |
| 10.5 | 0.55 | 31.41 | 481.94 | 588.61 |
| 11 | 0.59 | 33.70 | 469.82 | 626.59 |
| 11.5 | 0.63 | 36.05 | 456.59 | 664.56 |
| 12 | 0.67 | 38.47 | 442.15 | 702.54 |
| 12.5 | 0.72 | 40.97 | 426.38 | 740.51 |
| 13 | 0.76 | 43.57 | 409.11 | 778.49 |
| 13.5 | 0.81 | 46.30 | 390.17 | 816.46 |
| 14 | 0.86 | 49.16 | 369.28 | 854.44 |

These calculations are theoretical and based on the yield strength (2% elongation) of a 1.3 mm pin in double shear which is approximately 564.7 lbs. As can be seen, the required deployment force decreases as the link angle α increases, and the allowable vertebral member load increases as the link angle α increases.

FIGS. 6 and 7 illustrate another embodiment of the spacer 10. FIG. 6 illustrates the spacer 10 in a closed orientation. The overall shape of the spacer 10 is cylindrical and includes a nose 34 having a rounded front to ease insertion into the patient. The spacer 10 includes linkages 40, a pair of plates 50, and a pull arm 30 including the nose 34. A proximal section 39 forms part of the spacer 10. In one embodiment, plates 50 have a length less than the overall spacer length. Linkages 40 include teeth 44 at each end, and a pair of apertures 42 for receiving pins 62. Nose 34 and proximal section 39 include recesses 31 in which the linkages 40 are positioned. In one embodiment, linkages 40 and plates 50 have a rounded surface to conform to the cylindrical shape. In another embodiment, linkages 40 and plates 50 have a flat exterior surface. In the closed orientation, the link angle α is 0°.

FIG. 7 illustrates the spacer 10 in the opened orientation. Teeth 44 of opposing linkages 40 mate together as the spacer 10 opens. Nose 34 is connected to a pull arm 30. An axial force applied to the pull arm 30 forces the nose 34 inward towards the delivery device 80. The movement of the nose 34 causes the linkages 40 to move resulting in plates 50 moving outward from the centerline C of the spacer 10. The pull arm 30 may be axially moved a variety of distances to control the height of the spacer 10.

In embodiments illustrated in FIGS. 6 and 7, linkages 40 do not connect directly to the pull arm 30. Linkages 40 connect to the nose 34 which is connected to the pull arm 30. Movement of the nose 34 causes movement of the linkages 40. The proximal linkages 40 may or may not be directly or indirectly connected to the pull arm 30. In one embodiment, proximal linkages 40 are directly connected to the pull arm through pins.

In one embodiment, the linkages 40 connect to a middle section of the plates 50 adjacent to a mid-point M of the length. In another embodiment, linkages 40 connect to the plates 50 towards the ends distanced away from the mid-point M. In another embodiment, two linkages 40 connect at different positions along the plates 50 relative to the mid-point M (i.e., linkages 40 are not evenly spaced from the mid-point M). By way of example, a first linkage 40 connects at a position near the distal end of the plate 50 a distance x from the mid-point M, and a second linkage 40 connects adjacent to the mid-point of the plate 50 at a distance x less y from the mid-point. The plates 50 may be parallel to the centerline C, or angled in either direction relative to the centerline C.

Figure 8:
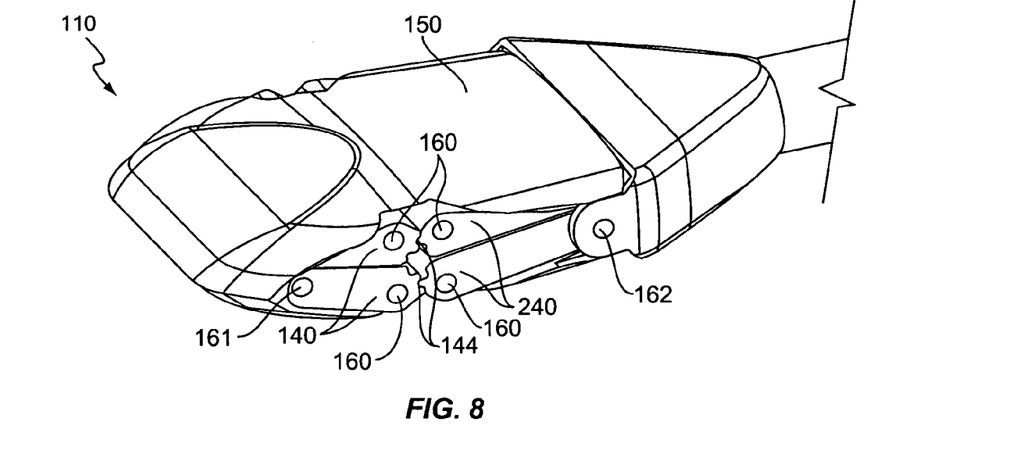
FIG. 8 is a perspective view of another spacer embodiment in a closed orientation.
Figure 9:
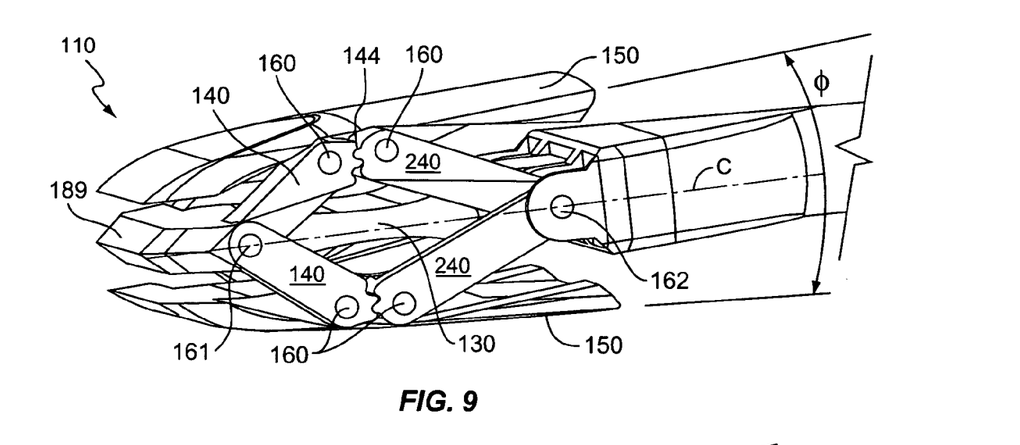
FIG. 9 is a perspective view of the spacer of FIG. 8 in a partially-open orientation.
Figure 10:
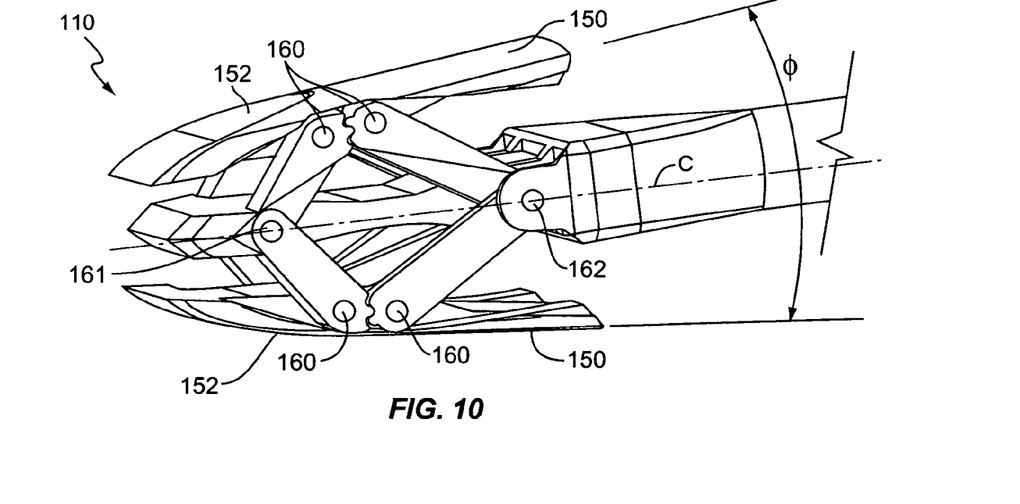
FIG. 10 is a perspective view of the spacer of FIG. 9 in an open orientation.

FIGS. 8, 9, and 10 illustrate another embodiment having first linkages 140 with a different length than second linkages 240. First and second linkages 140, 240 each extend between the pull arm 130 and plate 150. Pin 161 attaches a first end of the first linkages 140 to the pull arm 130, and pin 162 attaches a first end of the second linkages 240 to the pull arm 130. Pins 160 connect the second ends of the linkages 140, 240 to the plates 150. Teeth 144 at the second ends of the linkages 140, 240 mate together as the spacer 110 moves between open and closed orientations.

Plates 150 each have curved contact surfaces 152. In one embodiment, the curvature has a radius of about 100 mm to fit the concave shape of the endplates of the vertebral members. A distal end 189 of the pull arm 130 has an angled configuration that compliments the curvature of the plates 150. The combination of the distal end 189 and curved plates 150 give the spacer 110 a bullet shape in the closed orientation as illustrated in FIG. 8. In one embodiment, the spacer 110 has a length of about 30 mm, and a width of about 27 mm.

Varying the ratios of the link lengths controls the amount of lordotic angle θ formed by the plates 150 during deployment. The greater the differences in lengths, the greater the lordotic angle as the spacer 110 is deployed. In one embodiment, the length of the distal linkages 140 is about 7.4 mm, and the length of the proximal linkages 240 is about 12 mm. The height of the spacer 110 also increases with the deployment. The height is measured from the peak of curvature of the plates 150. FIGS. 8, 9, and 10 illustrate the changes in height and lordotic angle θ during deployment of the spacer 110.

FIG. 8 illustrates the spacer 110 in the closed orientation. In one embodiment, the height is about 8.4 mm. In the closed orientation, the lordotic angle is about 0° with the plates 150 being substantially parallel.

FIG. 9 illustrates a partial deployment of the spacer 110. The pull arm 130 has been moved proximally inward (i.e., to the right as illustrated in FIG. 9) thus pulling pin 161 inward and causing pin 162 to slide along the slot 37 (not illustrated) centered on the centerline C. In this embodiment, the height is about 13.8 mm, and the lordotic angle θ is between about 8.4°–8.6°.

FIG. 10 illustrates the spacer 110 in a fully-deployed orientation. The pull arm 132 and pin 161 have been moved further in the proximal direction. Pin 162 has continued to slide towards a distal section of slot 37. Plates 150 have continued to move outward with the lordotic angle θ increasing to about 15°–15.3°, and the height about 16.8 mm.

Figure 11:
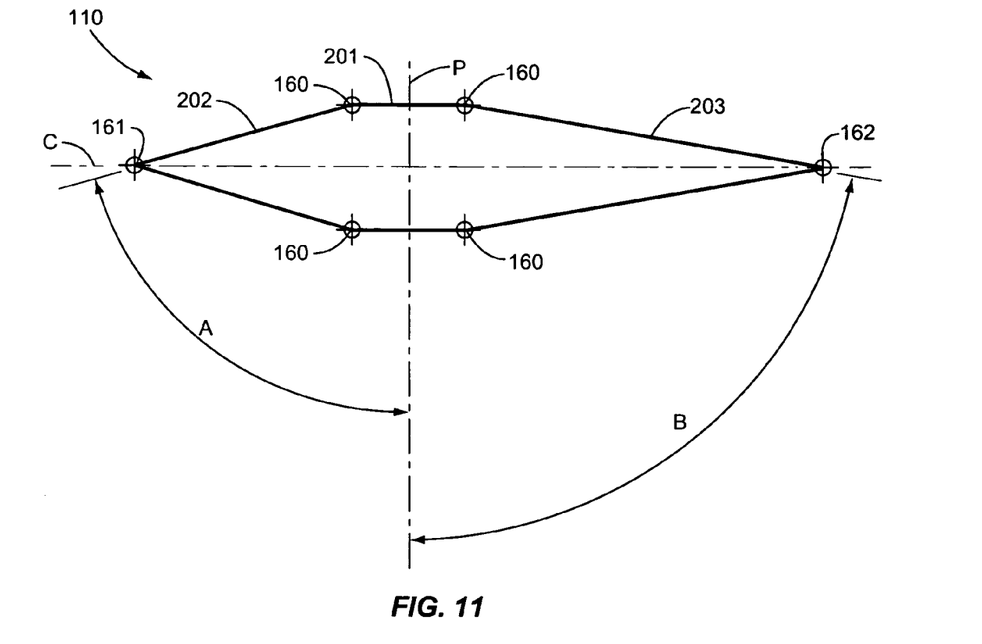
FIG. 11 is a schematic diagram corresponding to the spacer of FIG. 8 in the closed orientation illustrating the angles formed between a distal link and a proximal link.
Figure 12:
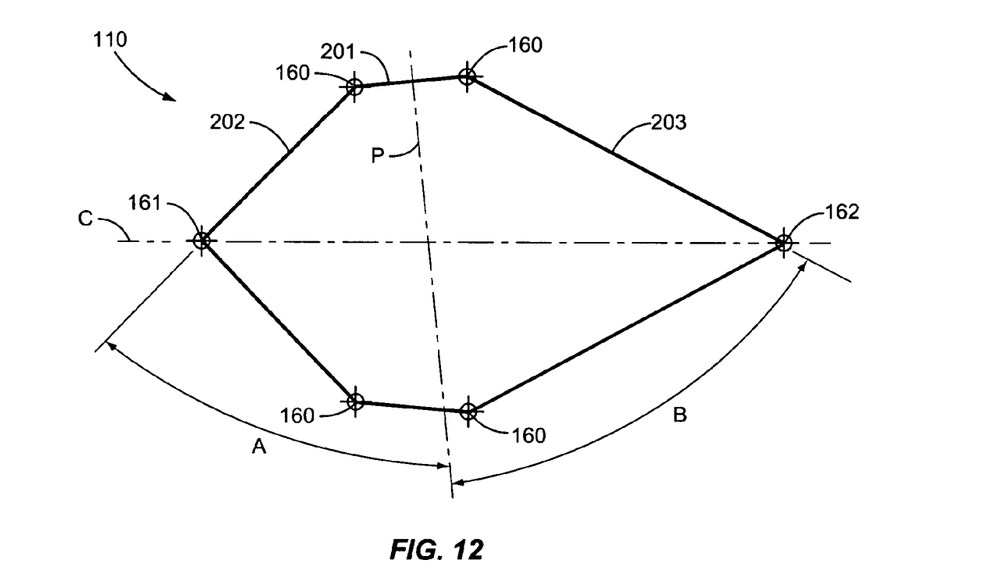
FIG. 12 is a schematic diagram corresponding to the spacer of FIG. 9 in the partially-opened orientation illustrating the angles formed between a distal link and a proximal link.
Figure 13:
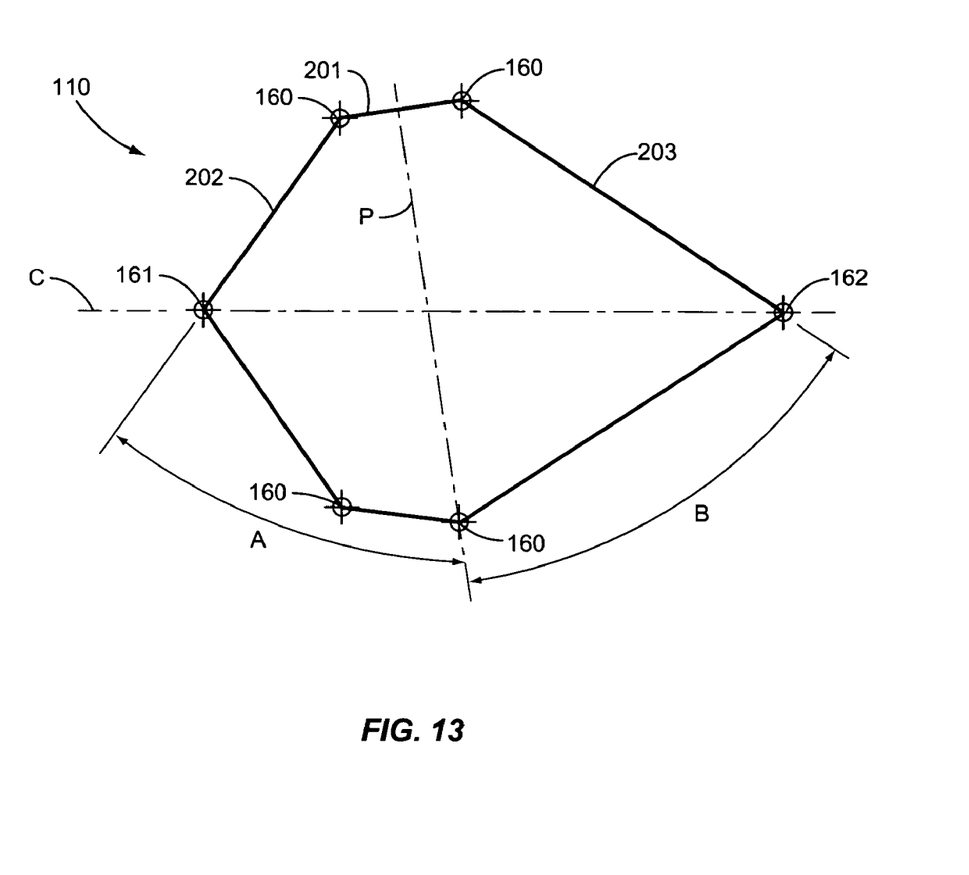
FIG. 13 is a schematic diagram corresponding to the spacer of FIG. 10 in the open orientation illustrating the angles formed between a distal link and a proximal link.

FIGS. 11, 12, and 13 schematically illustrate the movement of the linkages 140, 240 as the spacer 110 moves between closed and open orientations. FIG. 11 schematically illustrates the spacer 110 in the closed orientation (as shown in FIG. 8). As illustrated in FIG. 11, line 201 extends between a mid-point of the pins 160 that connect the upper plate 150 to the linkages 140, 240. A line P is perpendicular to line 201. Line 202 extends between a mid-point of pin 161 and a mid-point of pin 160 that connects the distal linkage 140 to the upper plate 150. Line 203 extends between a mid-point of pin 162 and the mid-point of pin 160 that connects the proximal linkage 240 to the upper plate 150. A first angle A is formed between the line 202 and line P. A second angle B is formed between the line 203 and line P. In the closed orientation, line P is perpendicular to the centerline C, and the lordotic angle is 0°. In one embodiment, the distal linkages 140 are about 7.4 mm, the proximal linkages 240 are about 12 mm, and the distance between the pins 160 is about 3.75 mm.

In an embodiment with the distal linkages 140 shorter than the proximal linkages 240, a difference exists between larger angle B and smaller angle A. The formula explaining the angles is defined as:

$$\text{Angle } B = \text{Angle } A + \text{Difference} \quad \text{(Eq 1)}$$

In one embodiment with distal linkage 140 being about 7.4 mm and the proximal linkages 240 about 12 mm, the angle A is about 73.2°, angle B is about 79.6°, and the difference is about 6.4°.

FIG. 12 schematically illustrates the spacer 110 in a partially-deployed orientation (as shown in FIG. 9). The orientation of line 201 has changed as the relative distance changes between pins 161, 162 during deployment. Line P that is perpendicular to line 201 also changes accordingly. Angle A formed between line 202 and line P has decreased, and angle B formed between line 203 and line P has also decreased. However, the difference between the two angles has remained the same and Equation 1 remains true. This is caused because the linkages 140, 240 are meshed together at a point adjacent to the plate 150. In the specific embodiment, angle A is about 49.7°, Angle B is about 56.3°, and the difference is about 6.4°.

FIG. 13 schematically illustrates the spacer 110 in the open orientation (as shown in FIG. 10). Pins 161 and 162 have moved relatively closer along the centerline C. Angle A and Angle B have each decreased from the partially opened orientation, and line P is further offset relative to centerline C. Again, the difference between angles A and B has remained the same. In the specific embodiment, angle A is about 42.6°, angle B is about 49°, and the difference is about 6.4°.

In one embodiment, the angles formed on a lower section of the spacer 110 also follow the parameters of Equation 1. In an embodiment with longer distal linkages 140 than proximal linkages 240, angle A is greater than angle B by the constant difference.

In the embodiments illustrated, the lordotic angle was about 0° when the spacer 110 is in the closed orientation. The lordotic angle may be an amount other than 0° in the closed orientation. Also, the embodiments illustrated include the first linkages 140 towards the distal end of the spacer 110 having a smaller length. In other embodiments, the first linkages 140 have a greater length than the proximal second linkages 240.

In one embodiment, the lordotic angle is determined by the edges of the plates 140, 240. In another embodiment, the lordotic angle is determined by twice the angle formed by line 201 and the centerline C. Embodiments are also contemplated in which the spacer 110 includes only a single moving plate. In these embodiments, the lordotic angle is the angled formed by line 201 and the centerline C.

FIG. 14 illustrates an alternative embodiment of the pins 62, 86. A push link 97 is positioned within the slot 37 of the pull arm 30. The push link 97 includes pins 62 and 86 that mount to the linkages 40 and delivery device 80 respectively. Push link 97 is sized to slide within the slot 37 during movement of the pull arm 30. In one embodiment, push link 97 has an "H" shape with a first set of pins (62, 86) extending on a first side of the device to connect the delivery device 80 and the first set of proximal links, with a second set of pins extending on a second side to connect the delivery device and the second set of proximal links.

In another embodiment (not illustrated), pin 62 does not extend through the pull arm 30. A first pin on a first lateral side of the pull arm 30 attaches together two of the proximal linkages, and a second pin on a second lateral side of the pull arm 30 attaches together the other two proximal linkages. In this embodiment, the two pins may be connected to the delivery device 80.

The term vertebral member is used generally to describe the vertebral geometry comprising the vertebral body, pedicles, lamina, and processes. The spacer 10 may be sized and shaped, and have adequate strength requirements to be used within the different regions of the vertebra including the cervical, thoracic, and lumbar regions. In one embodiment, spacer 10 is positioned within the disc space between adjacent vertebra. Plates 50 contact the end plates of the vertebra to space the vertebra as necessary. In one embodiment, the spacer 10 is inserted posteriorly in the patient. In another embodiment, the spacer 10 is inserted from an anteriorly into the patient. In another embodiment, the spacer is inserted laterally into the patient.

In another embodiment (not illustrated), spacer 10 includes only one moving plate 50. A first plate is attached to the linkages 40 and moves as discussed above. A second plate is stationary. The linkages 40 move outward from the stationary plate to expand the height of the spacer 10 to the open orientation. This embodiment may include any number of linkages 40 depending upon the desired spacing and strength requirements.

The present invention may be carried out in other specific ways than those herein set forth without departing from the scope and essential characteristics of the invention. In one embodiment, spacer 10 and delivery device 80 are constructed of stainless steel. The present embodiments are, therefore, to be considered in all respects as illustrative and not restrictive, and all changes coming within the meaning and equivalency range of the appended claims are intended to be embraced therein.

The invention claimed is:

1. A device to space vertebral members comprising:
   first and second linkages each having a first end and a second end with the second linkage having a different length than the first linkage;
   a pull arm pivotally connected to the first end of each of the first and second linkages; and
   a plate connected to the second end of each of the first and second linkages;
   the pull arm being positioned in a first orientation with the second ends spaced a first distance from the pull arm and the plate at a first angle relative to the pull arm, and a second orientation with the second ends spaced a greater distance from the pull arm than the first distance and the plate at a second angle relative to the pull arm at an angle greater than the first angle.

2. The device of claim 1, wherein the plate is substantially parallel with the pull arm in the first orientation.

3. The device of claim 2, wherein the second angle has a maximum range in the second orientation of about 7.5° measured between the plate and a centerline.

4. The device of claim 1, wherein a pin connects the first end of the second linkage to the pull arm and extends through an elongated slot in the pull arm.

5. The device of claim 1, wherein teeth are positioned at the second ends of the first and second linkages, with the second end of the first linkage mating with the second end of the second linkage.

6. The device of claim 1, further comprising an elongated delivery device to position the device between the vertebral members.

7. The device of claim 6, wherein the elongated delivery device is detachable from the device.

8. The device of claim 1, wherein the second linkage is proximally positioned relative to the first linkage and is longer than the first linkage.

9. The device of claim 1, wherein a first pin attaches the first linkage to the plate and a second pin attaches the second linkage to the plate, with the first pin being spaced apart from the second pin.

10. The device of claim 1, further comprising a push link positioned within the pull arm having a first pin that attaches to the second linkage and a second pin that attaches to a delivery device.

11. A device to space vertebral members comprising:
a first plate and a second plate;
a first linkage pair pivotally attached to the first plate and the second plate;
a second linkage pair pivotally attached to the first plate and the second plate, the second linkage pair being longer than the first linkage pair;
a first toothed end of the first linkage pair attached to the first plate mates with a first toothed end of the second linkage pair, and a second toothed end of the first linkage pair attached to the second plate mates with a second toothed end of the second linkage pair when a distance between the first plate and the second plate increases and an angle formed between the first plate and the second plate changes.

12. The device of claim 11, wherein a total of four linkage pairs are positioned between the first plate and the second plate.

13. A device to space vertebral members comprising:
a first plate;
a second plate;
a pull arm positioned between the first plate and the second plate;
a first linkage pair and a second linkage pair each comprising a first end connected to the first plate, a second end connected to the second plate, the first linkage pair connected to the pull arm at a first connection point, and the second linkage pair connected to the pull arm at a second connection point, the first linkage pair having a different length than the second linkage pair;
the device positionable between a first orientation having a first height and a second orientation having a second height greater than the first height, a distance between the first connection point and the second connection point being greater in the first orientation than in the second orientation and an angle formed between the plates being different in the first orientation and the second orientation.

14. The device of claim 13, wherein the pull arm further comprises an elongated slot sized to receive a pin to attach the second linkage pair to the pull arm, the pin positioned at a first position along the elongated slot at the first orientation, and a second position along the elongated slot at the second orientation.

15. The device of claim 14, further comprising a push link positioned within the elongated slot, the push link comprising the pin to attach the second linkage pair to the pull arm, and a second pin to attach to a delivery device.

16. The device of claim 14, wherein the first linkage pair is connected to the pull arm with the first connection point being at the same position relative to the pull arm at the first orientation and the second orientation.

17. The device of claim 13, wherein the first linkage pair is shorter than the second linkage pair, and the angle formed between the plates is greater in the second orientation than at the first orientation.

18. The device of claim 13, the first plate is substantially parallel to the second plate in the first orientation.

19. The device of claim 13, wherein teeth at the first and second ends of each the first linkage pair and the second linkage pair operatively connect the first linkage pair with the second linkage pair.

* * * * *